(12) United States Patent
Massaro (10) Patent No.: US 10,306,875 B1
(45) Date of Patent: Jun. 4, 2019

(54) DISPOSABLE CONTAINER FOR THE MASS-REARING OF INSECTS

(71) Applicant: Verily Life Sciences LLC, Mountain View, CA (US)

(72) Inventor: Peter Massaro, Belmont, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 228 days.

(21) Appl. No.: 15/285,642

(22) Filed: Oct. 5, 2016

(51) Int. Cl.
| | |
|---|---|
| *A01K 67/033* | (2006.01) |
| *B29C 51/10* | (2006.01) |
| *B29K 67/00* | (2006.01) |
| *B29K 105/00* | (2006.01) |
| *B29K 9/00* | (2006.01) |

(52) U.S. Cl.
CPC ............ *A01K 67/033* (2013.01); *B29C 51/10* (2013.01); *B29K 2009/00* (2013.01); *B29K 2067/046* (2013.01); *B29K 2105/256* (2013.01); *B29K 2995/006* (2013.01); *B29K 2995/0065* (2013.01)

(58) Field of Classification Search
CPC .................................................. A01K 67/033
USPC .......................................................... 119/635
See application file for complete search history.

(56) References Cited

U.S. PATENT DOCUMENTS

| | | | |
|---|---|---|---|
| 3,223,237 A | 12/1965 | Stevens et al. | |
| 3,468,289 A * | 9/1969 | Broida | B65D 25/14 |
| | | | 119/496 |
| 3,750,625 A | 8/1973 | Edwards | |
| 4,212,267 A | 7/1980 | Patterson | |
| 4,368,690 A | 1/1983 | Tenzer | |
| 4,417,545 A * | 11/1983 | Finney | A01K 67/033 |
| | | | 119/6.6 |
| 4,646,683 A * | 3/1987 | Maedgen, Jr. | A01K 67/033 |
| | | | 119/6.5 |
| 4,765,275 A * | 8/1988 | Yukawa | A01K 67/033 |
| | | | 119/6.5 |
| 4,785,764 A * | 11/1988 | Muller | A01K 67/033 |
| | | | 119/416 |
| 4,863,693 A | 9/1989 | Howell | |

(Continued)

FOREIGN PATENT DOCUMENTS

| | | |
|---|---|---|
| CN | 102499182 | 6/2012 |
| CN | 202285912 | 7/2012 |

(Continued)

OTHER PUBLICATIONS

U.S. Appl. No. 15/285,623, Notice of Allowance dated Apr. 16, 2018, 9 pages.

(Continued)

*Primary Examiner* — Yvonne R Abbott-Lewis
(74) *Attorney, Agent, or Firm* — Kilpatrick Townsend & Stockton LLP (57) ABSTRACT

A disposable container for the mass-rearing of insects can include a first layer, a mixture, and a second layer. The first layer can be molded to form a cavity and define an opening to allow the mixture to be positioned in the cavity. A quantity of the mixture can be positioned in the cavity and comprise insect larvae and food for the insect larvae. The second layer can be positioned over the opening and coupled to the first layer to seal the opening. The first layer or the second layer can include a disposable material and the second layer can couple to the first layer to form a disposable container.

20 Claims, 4 Drawing Sheets

(56) References Cited

U.S. PATENT DOCUMENTS

| | | | |
|---|---|---|---|
| 5,074,247 A * | 12/1991 | Gupta | A01K 1/031 119/452 |
| 5,178,094 A | 1/1993 | Carr et al. | |
| 5,351,643 A | 10/1994 | Hughes | |
| RE35,348 E * | 10/1996 | Georgi | A01K 67/033 119/6.6 |
| 5,594,654 A | 1/1997 | Shuman et al. | |
| 5,784,991 A * | 7/1998 | Ukishiro | A01K 67/033 119/6.5 |
| 5,819,685 A * | 10/1998 | Kappelt | A01K 67/033 119/6.5 |
| 6,244,213 B1 | 6/2001 | Tedders et al. | |
| 6,293,223 B1 * | 9/2001 | Blossey | A01K 67/033 119/6.5 |
| 6,557,487 B1 * | 5/2003 | Fleischmann | A61K 35/63 119/6.5 |
| 6,688,255 B2 | 2/2004 | Donaldson et al. | |
| 6,766,251 B2 | 7/2004 | Mafra-Neto et al. | |
| 7,861,672 B2 | 1/2011 | Power | |
| 8,322,304 B2 * | 12/2012 | Chung | A23K 50/90 119/6.5 |
| 9,510,572 B2 * | 12/2016 | Aldana | A01K 67/033 |
| 9,642,344 B2 | 5/2017 | Unger | |
| 2002/0185605 A1 | 12/2002 | Shuman et al. | |
| 2006/0196427 A1 | 9/2006 | Lepori | |
| 2012/0017834 A1 | 1/2012 | Holland et al. | |
| 2013/0083974 A1 | 4/2013 | Tsai et al. | |
| 2013/0204581 A1 | 8/2013 | Park et al. | |
| 2013/0319334 A1 | 12/2013 | Newton et al. | |
| 2014/0123902 A1 | 5/2014 | Kitazumi et al. | |
| 2018/0092339 A1 | 4/2018 | Massaro et al. | |

FOREIGN PATENT DOCUMENTS

| | | |
|---|---|---|
| CN | 105409893 | 3/2016 |
| WO | 2010038055 | 4/2010 |
| WO | 2015126855 | 8/2015 |
| WO | 2016024164 | 2/2016 |

OTHER PUBLICATIONS

Carvalho et al., "Mass production of genetically modified Aedes aegypti for field releases in Brazil", Journal of visualized experiments: JoVE 83 (2014).

International Application No. PCT/US2017/054094, "International Search Report and Written Opinion", dated Nov. 29, 2017, 12 pages.

U.S. Appl. No. 16/055,253, "Non Final Office Action", Sep. 21, 2018, 6 pages.

* cited by examiner

DISPOSABLE CONTAINER FOR THE MASS-REARING OF INSECTS

TECHNICAL FIELD

The present disclosure relates generally to the mass-rearing of insects. More specifically, but not by way of limitation, this disclosure relates to a disposable container for use in the mass-rearing of insects.

BACKGROUND

The mass-rearing of insect larvae can be very labor intensive. A lab technician may manually add a number of eggs or insect larvae to a plastic tray and determine the amount of food and water to add into the tray for the insect larvae. The lab technician may hand carry the plastic tray to a storage area to store the plastic tray. Periodically, the lab technician may perform observations on the insect larvae in the plastic tray and add food and water as needed. After the insects are released, the plastic trays can be cleaned and sterilized before being re-used. The cleaning processes can be labor intensive and include a contamination risk in subsequent uses of the tray.

SUMMARY

Various examples are described for a disposable container for the mass-rearing of insects. For example, one disclosed disposable container for the mass-rearing of insects includes a first layer, a quantity of mixture, and a second layer. The first layer can be molded to form a cavity and define an opening to allow a mixture to be positioned in the cavity. The quantity of mixture can be positioned in the cavity and can include insect larvae and food for the insect larvae. The second layer can be positioned over the opening and coupled to the first layer to seal the opening. The first layer or the second layer can include a disposable material and the second layer can be coupled to the first layer to form the disposable container for the mass-rearing of insects.

One disclosed method for assembling a disposable container for the mass-rearing of insects includes providing a first layer to be molded to form a cavity and define an opening to allow a mixture to be positioned in the cavity. The method can also include providing a quantity of the mixture to be positioned in the cavity. The mixture can include insect larvae and food for the insect larvae. The method can also include providing a second layer to be positioned over the opening and coupled to the first layer for sealing the opening and to form a disposable container for the mass-rearing of insects.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

DETAILED DESCRIPTION

Certain aspects and features relate to a disposable container for the mass-rearing of insects. A disposable container within the context of this specification means a container that is created to be discarded after a single use, rather than cleaned and sterilized for re-use. Thus, examples of disposable containers can be made of inexpensive materials using an automated process to reduce per-unit costs of the disposable containers. Such materials can include, but are not limited to, thermoplastics (e.g., polyethylene or polypropylene), polyisoprene, paper pulp, polystyrene, or ceramics. In some examples, the disposable container is a form-filled sealed bag. The disposable container can include a plastic layer that is molded to form a cavity that can retain a mixture for the mass-rearing of insects. Another plastic layer can be coupled to the plastic layer to seal the cavity.

In some aspects, the disposable container can include one or more posts extending from one plastic layer to the other plastic layer within the cavity to provide structural support for the container to allow the container to be transported via an automated rearing system, e.g., using a robotic arm, without collapsing. The posts can be formed by vacuum molding one of the plastic layers using a mold having and interior space with one or more projections over which the posts are formed. The posts can then be sealed to the other plastic layer to create a strengthened internal structure for the container.

In some aspects, an amount of a mixture of water, food, and insect eggs or larvae can be deposited into the cavity where they can develop and mature into adult insects. An appropriate amount of the mixture to be deposited within the cavity can be determined by determining the volume of the disposable container and a desired air gap between the upper surface of the mixture and the upper surface of the disposable container. For example, the size of the air gap can be determined based on the type of insects being reared, and amount of air for the larvae to breathe, and to provide room for maturing insects to develop. Suitable air gaps may be between approximately 1/16 of an inch to 2 inches in some examples. One or more of the plastic layers can be gas permeable to allow air to pass in and out of the cavity, while also preventing the mixture from leaking from the disposable container. One or more of the plastic layers can be transparent or translucent to allow observation of the insects and the growth of the insects.

In some aspects, the disposable container can also serve as a release container. For example, a disposable container can be biodegradable and positioned in a release environment, such as an outdoor area or an enclosure for performing tests on the insects. A biodegradable material (e.g., a material capable of being decomposed by bacteria or other living organisms) can be used such that the disposable container remains sealed until the insects have matured and releases the insects as the disposable container biodegrades. For example, a disposable container can be made of polylactic acid, which can decompose into compostable material after prolonged exposure to heat. Although the examples herein describe a disposable container made of plastic, a disposable container can be made of any suitable disposable material. For example, a disposable container for rearing mosquitos can be made of cornstarch and positioned in the wild to release the mature mosquitos and biodegrade.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative aspects but, like the illustrative aspects, should not be used to limit the present disclosure.

Figure 1:
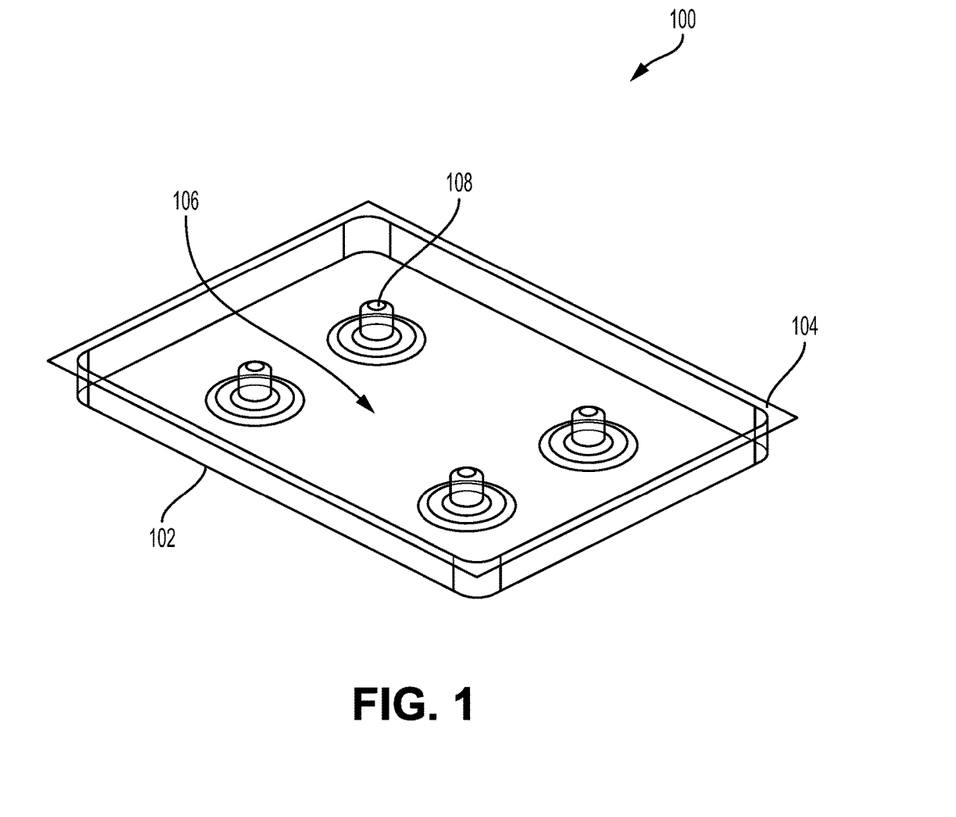
FIG. 1 is a perspective view of an example of a disposable container for the mass-rearing of insects according to one aspect of the present disclosure.
Figure 2:
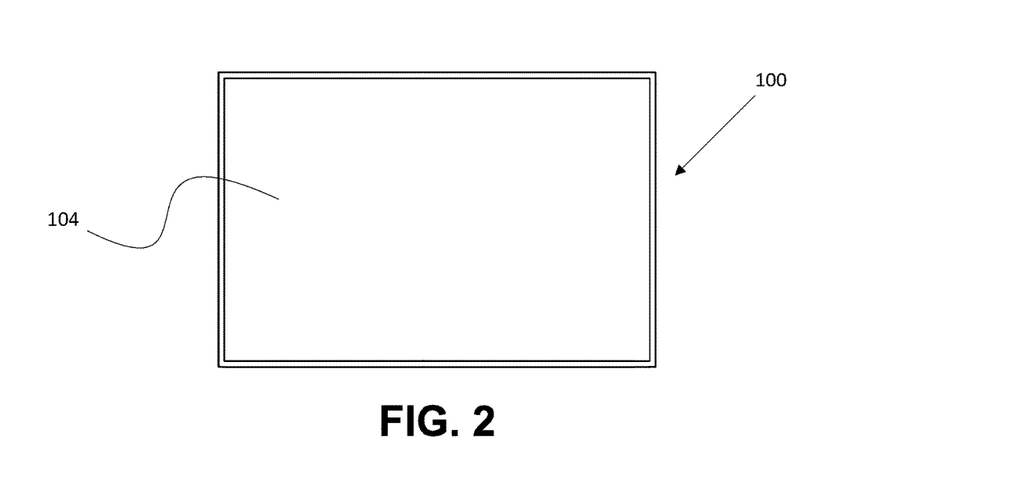
FIG. 2 is a top view of an example of a disposable container for the mass-rearing of insects according to one aspect of the present disclosure.
Figure 3:
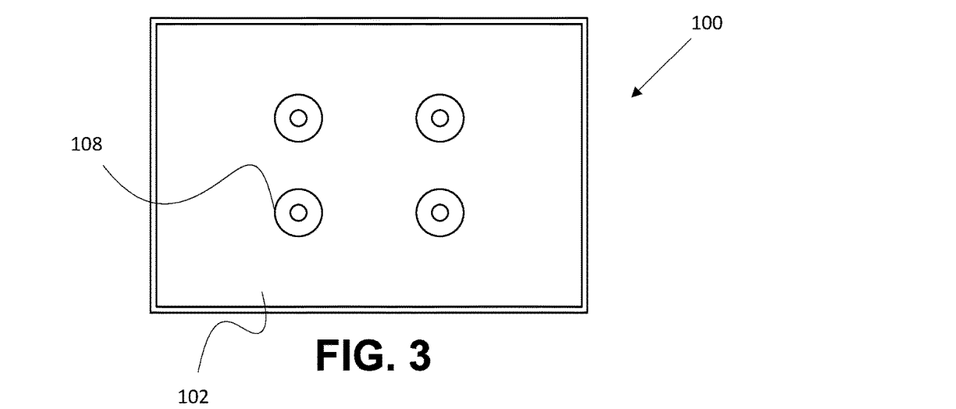
FIG. 3 is a bottom view of an example of a disposable container for the mass-rearing of insects according to one aspect of the present disclosure.
Figure 4:
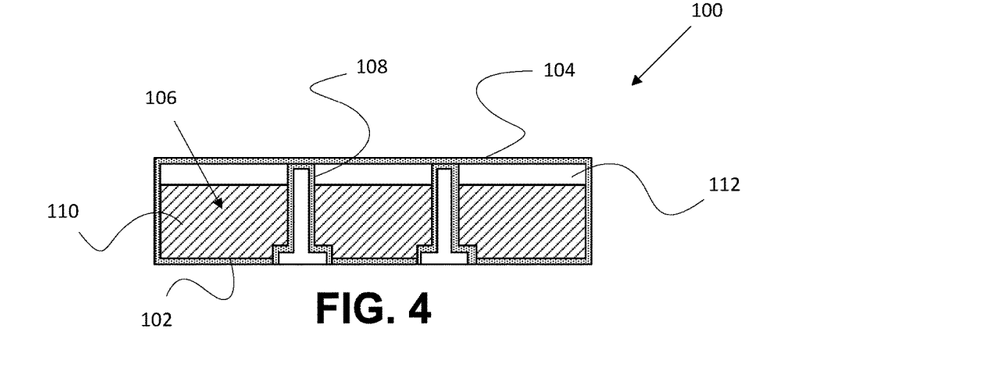
FIG. 4 is a cross-sectional side view of an example of a disposable container for the mass-rearing of insects according to one aspect of the present disclosure.

FIGS. 1-4 depict a perspective view, top view, bottom view, and cross-sectional side view respectively of an example of a disposable container 100 for the mass-rearing of insects. In this example, the disposable container 100 has a bottom layer 102, which defines a cavity 106, and a top layer 104 coupled to the bottom layer 102 around an edge of the cavity 106. In this example, the bottom layer also defines four posts 108, which extend upward from the bottom layer 102, through the cavity 106, and are coupled to the top layer 104. The example disposable container 100 shown in FIG. 1 is also partially filled with a mixture of water, food, and insect larvae, with an air gap formed between the surface of the mixture and the top layer 104.

In this example, the disposable container 100 is approximately 11 inches wide, 15 inches long, and 2 inches deep with 1-inch diameter posts and a half-inch air gap. In other examples, the disposable container may be larger to fill a storage unit (e.g., a storage shelf or a storage tray) or the disposable container may be smaller to be modular and more easily transported. A height of the air gap can be proportional to the size of the disposable container or the height of the air gap can be calculated based on the type of insect being reared in the disposable container. The plastic used in this example has a thickness of less than 250 microns.

While this example shows a disposable container having four posts 108 formed in the bottom layer 102, other examples may have more or fewer posts 108, or may not have any posts 108 at all. Further, while this example shows the posts 108 formed in the bottom layer 102, in other examples, the posts 108 may be formed in the top layer 104, or both the top and bottom layers 102, 104. Further, while the posts 108 shown in FIG. 1 extend through the entire height of the cavity 106, other examples may include one or more posts 108 that only extend through a portion of the cavity 106. For example, each of the top and bottom layers 106 may have posts 108 formed in them that extend halfway into the container such that corresponding posts in the top and bottom layers may be coupled to each other. Further, while the posts 108 shown in FIG. 1 are generally cylindrical, the posts 108 may have other shapes or sizes in other examples, such as generally conical shapes, wall or planar shapes, etc.

In some aspects, the bottom layer 102 can be constructed from a plastic film that has been molded to create the cavity 106. For example, the cavity 106 can be created by heating a portion of the bottom layer 102 and then shaping the cavity 106 by blowing the bottom layer 102 over a mold. In additional or alternative examples, the bottom layer 102 can be blown to create the cavity 106. In some examples, as discussed above, the bottom layer 102 can also be molded to create the posts 108. In some examples, a mold for the bottom layer may comprise a lower surface having one or more protrusions extending upward over which the bottom layer may be blown to form one or more posts. In some aspects, the posts 108 can be arranged to allow movement of the mixture between the posts 108. In additional or alternative aspects, the bottom layer 102 can be molded to form additional structural components. In some example, the bottom layer 102 can be molded to create walls that form interior compartments in the disposable container 100 as well as increased rigidity of the disposable container 100. In additional or alternative examples, the bottom layer 102 can be molded to include different surfaces for aiding growth of the insects during different periods of the growth cycle of the insects. For example, the bottom layer 102 can be molded to form a cavity with sloped walls.

The bottom layer 102 and the top layer 104 can be brought into contact, and the bottom layer 102 or the top layer 104 can be heated to couple the bottom layer 102 and the top layer 104. For example, the top layer 104 can be lowered onto, and pressed against, the bottom layer 102 such that a heat source can weld the top layer 104 to the bottom layer 102. The heat source can weld the top layer 104 to the bottom layer 102 by melting a portion of the top layer 104 at an edge of the cavity 106 and allowing the top layer 104 to re-harden coupled to the bottom layer 102.

Coupling the bottom layer 102 and top layer 104 can seal the cavity 106. In some aspects, the posts 108 can be coupled to the top layer 104 to provide rigidity to the disposable container 100. In additional or alternative aspects, an adhesive (e.g., epoxies, pressure-sensitive adhesives, etc.) can be used to couple the top layer 104 and the bottom layer 102. For example, the adhesive can be applied to an upper surface of the bottom layer 102 around the edge of the cavity 106. A lower surface of the top layer 104 can be pressed against the upper surface of the bottom layer 102 and held until the adhesive sets.

In some aspects, a resealable opening can be formed in the disposable container 100 for subsequently adjusting the environment in the cavity 106. In some examples, the resealable opening can be formed by using a resealable adhesive to couple a portion of the top layer 104 to the bottom layer 102. In additional or alternative examples, a resealable fastener can be coupled to the top layer 104 or the bottom layer 102.

In some aspects, the bottom layer 102 and/or the top layer 104 can be transparent or translucent plastic films to allow observation of insects in the cavity 106. In additional or alternative aspects, the bottom layer 102 and/or the top layer 104 can be opaque plastic films to reduce or prevent a portion of the light spectrum from entering the cavity. In some aspects, the bottom layer 102 can be molded and sealed to the top layer 104 by a standard form-filled packaging machine.

As discussed above, the disposable container 100 can be made of inexpensive materials to reduce the costs to make each container. This allows the containers to be used a single time, thereby potentially eliminating contamination risks associated with cleaning rearing containers. Rather than spending resources to sterilize a used disposable container, the used disposable container can be replaced by a new disposable container. Discarding a used disposable container can reduce contamination risk by eliminating the possibility of remnants from a previous insect mass-rearing cycle remaining in a used disposable container and affecting a subsequent mass-rearing cycle. In some examples, a disposable container can be biodegradable with a life span greater than a mass-rearing cycle, such that after the disposable container has been used in a mass-rearing cycle the used disposable container biodegrades.

Figure 5:
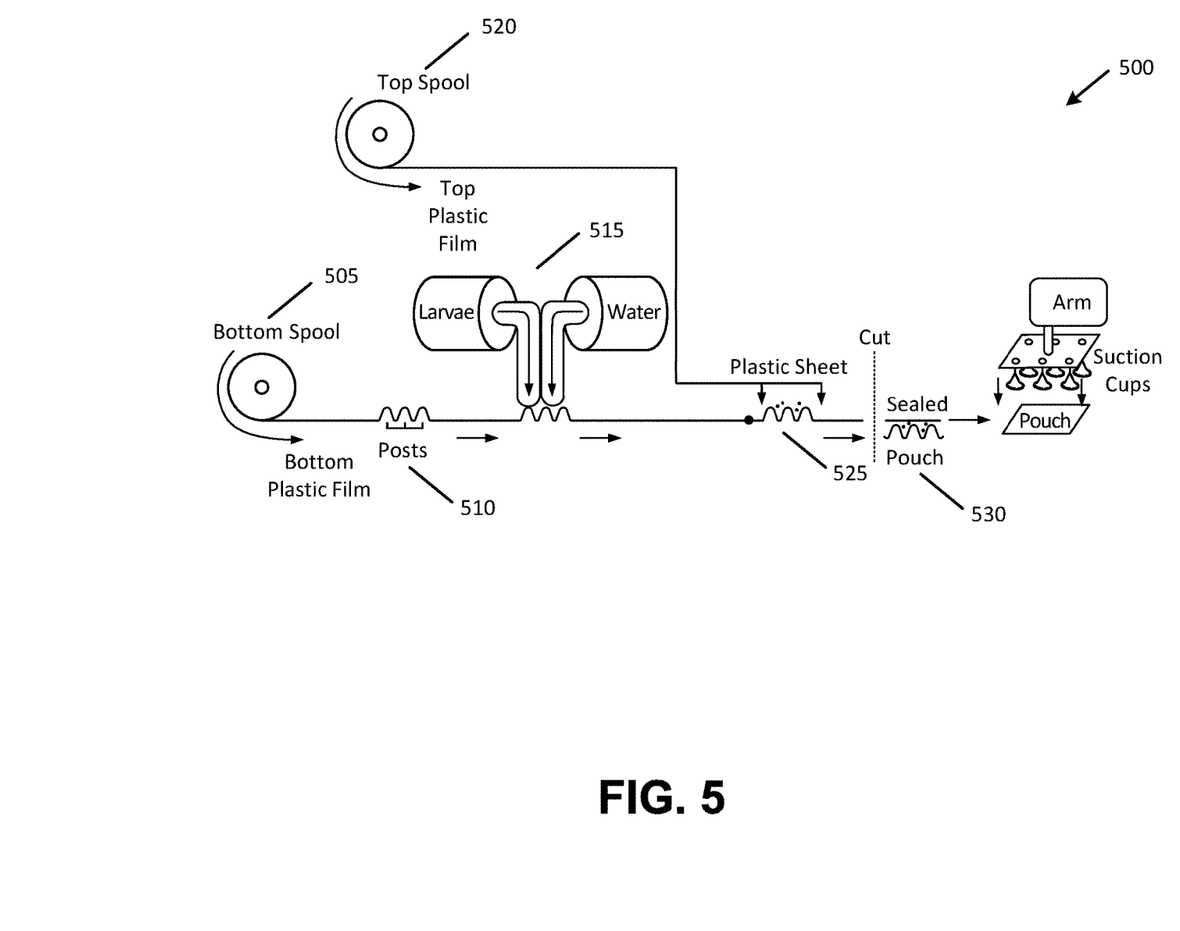
FIG. 5 is a flow diagram of an example of a process for manufacturing a disposable container for the mass-rearing of insects according to one aspect of the present disclosure.

FIG. 5 is a flow diagram of a process 500 for manufacturing a disposable container for the mass-rearing of insects. In some aspects, the process 500 can be performed as part of an automated mass-rearing system that produces disposable containers for the mass-rearing of insects and monitors the disposable containers as the insects are reared.

In stage 505, plastic film (e.g., a polyethylene film or a polylactic acid film) for use as a bottom layer of the disposable container can be dispensed from a spool of plastic. In some aspects, the plastic film can be dispensed on to a moving surface, such as a conveyor belt. In additional or alternative aspects, the plastic film can be positioned to move on a series of rollers that rotate to pull the plastic film from the spool. The plastic film can be heated and molded to form a cavity therein. In some examples, the cavity can be created by moving the plastic over an opening and moving the mold down to press the plastic into an opening and around a mold. In additional or alternative examples, the cavity can be vacuum formed by moving the film over a mold and applying a suction force to a portion of the heated plastic film to pull the plastic into the mold. In some aspects, the disposable containers can be liners for reusable containers for the mass-rearing of insects. In some examples, the plastic film can be stretched across a tray, and cavities can be formed as liners to compartments in the tray.

Although FIG. 5 depicts the disposable container being made of a plastic film, any non-toxic, inexpensive material can be used. In some examples, the material can include a thermoplastic, polyisoprene, paper pulp, polystyrene, or ceramic. In additional or alternative examples, the disposable containers are made of a biodegradable material (e.g., polylactic acid or cornstarch) that can be designed to degrade (e.g., decompose) after the insects have matured.

In stage 510, one or more posts can be formed from the bottom layer. In some aspects, the posts can be formed at substantially the same time as the cavity. The mold for forming the cavity can include protrusions such that applying a force to pull the bottom layer around the mold forms the posts as well as the cavity. In additional or alternative aspects, the posts can be formed in the bottom layer after the cavity is formed. The bottom layer can be reheated and air can be blown at certain portions of the bottom layer to create indentations that can extend through the cavity.

In some aspects, the posts can be formed throughout the bottom layer to support the cavity. For example, the posts can prevent a top layer from collapsing onto the mixture once the top layer is laid against the bottom layer. In additional or alternative examples, the posts can be positioned to provide greater support for the top layer when the disposable container is lifted by an arm using suction cups. The one or more posts can have any shape or size. In some aspects, the posts are approximately cylindrical or conical and are positioned to preserve a gap between the posts to avoid compartmentalizing the disposable container.

In stage 515, a quantity of a mixture can be dispensed into the cavity in the bottom layer. The mixture can include insect larvae, water, food, and other additives. In some aspects, chlorine or another chemical can be added to the mixture to sterilize the insects. In some aspects, the mixture can be added after the bottom layer and the top layer are partially coupled. The quantity of the mixture can be determined based on the type of insect and the desired population of insects to be reared. In some examples, the volume of the cavity can be calculated and a quantity of the mixture can be added such that an air gap remains between the surface of the mixture and the top layer of the disposable container. The air gap can allow insect larvae to breathe and to provide room for maturing insects to develop. The size of the air gap can be based on the type of insect being reared. For example, a disposable rearing container for mosquitos can have between approximately a ¼ to ½ inch, e.g., within ⅛ inch, air gap.

In stage 520, another plastic film for use as a top layer of the disposable container can be dispensed from another spool of plastic. The dispensed plastic film can then be routed to overlay the cavity and mixture to enable the plastic film to be sealed to the bottom layer.

In stage 525, the bottom layer and the top layer can be coupled to form the disposable container. A portion of the top layer or a portion of the bottom layer surrounding the cavity can be heated such that the portion of the top layer and the portion of the bottom layer are coupled (e.g., welded) together. In some aspects, an adhesive can be applied to a surface of the top layer or the bottom layer to couple the top layer to the bottom layer. For example, an adhesive can be applied to an upper surface of the bottom layer around the perimeter of the cavity. A lower surface of the top layer can then be pressed against the adhesive to form a seal and couple the bottom and top layers. In some aspects, one or more posts can also be coupled to the top plastic layer to improve the stability and rigidity of the disposable container.

The top layer or the bottom layer can be gas permeable such that the mixture is sealed in the cavity but air can circulate between the cavity and the area external to the disposable container. In some examples, the bottom layer can be gas permeable by being formed from a gas permeable material (e.g., polyisoprene). The gas permeable environment for larval rearing can keep out mold or bacterial and maintain consistency between disposable containers. Further, an air gap can be created in the bag to allow larvae to breathe from the air gap. By creating an air gap, the larvae can have a higher chance at staying viable.

In stage 530, the disposable container can be cut from the plastic film extending from the spools. In some aspects, the disposable containers can be transported to a release environment and used as release containers. The process 500 can also include storing the disposable containers in a storage unit. The storage unit can store the disposable containers in individual storage areas that can be temperature controlled to enable the insect larvae to grow quickly. The storage unit can also handle additional feeding cycles throughout the rearing process. The disposable containers can also be placed on a tray that can hold multiple disposable bags and can be stored in storage racks. In some examples, a disposable container can be tagged (e.g., barcoded) so that individual disposable containers can be tracked in a database.

Although process 500 depicts manufacturing disposable containers with posts, some process can manufacture disposable containers without posts. In some aspects, a process can produce disposable containers with posts extending from a top layer rather than the bottom layer. In additional or alternative aspects, a process can produce a series of disposable containers coupled together or as a liner for compartments in a tray.

Figure 6:
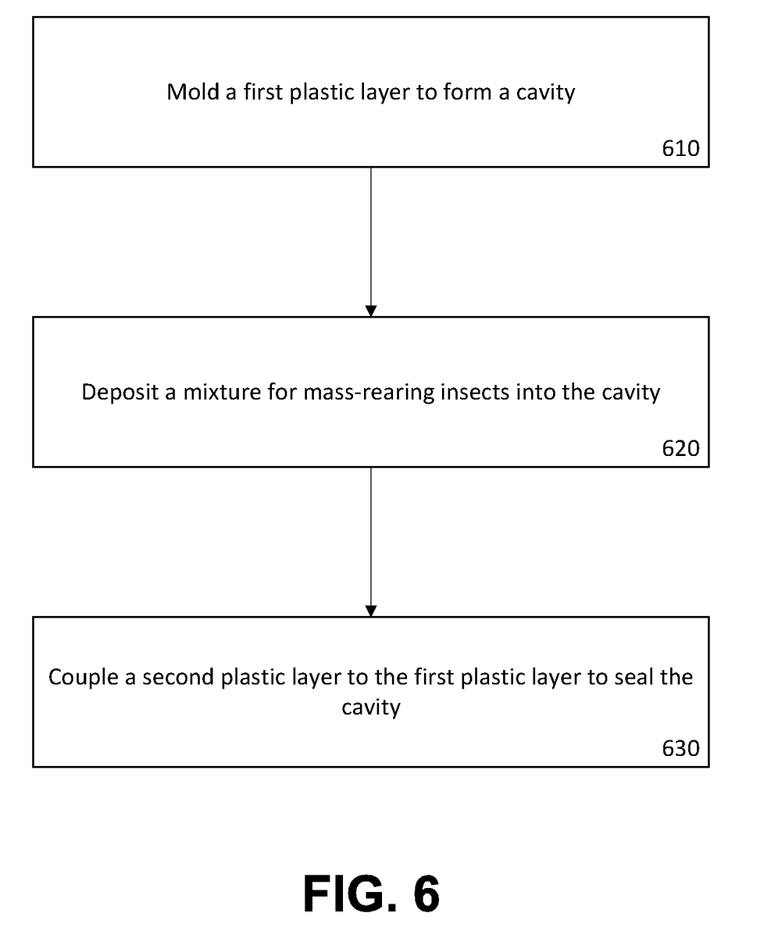
FIG. 6 is a flow chart of an example of a process for manufacturing a disposable container for the mass-rearing of insects according to one aspect of the present disclosure.

FIG. 6 is a flow chart of a process for manufacturing a disposable container for the mass-rearing of insects. In some examples, the process can be performed by one or more components of an automated process (e.g., process 500 in FIG. 5).

In Block 610, a first plastic layer is molded to form a cavity. In some aspects, a first plastic layer (e.g., a pliable film) can be dispensed from a spool. The first plastic layer can be heated to above approximately 110° C. and the cavity can be formed by displacing a portion of the first plastic layer. In some examples, heating the plastic can make the plastic more flexible, such that blowing air at a portion of the first plastic layer can produce the cavity. In additional or alternative examples, a vacuum can use suction to stretch the first plastic layer and form the cavity. In additional or alternative examples, the portion can be pressed into a mold. The high temperatures can sterilize the first plastic layer and prevent bacteria or mold from affecting the insect rearing.

In some aspects, one or more posts can be formed as the first plastic layer is molded to from the cavity. For example, blowing air at certain portions of the heated plastic layer can create indentations that can extend through the cavity. In other examples, the mold can contain projections such that the posts can be formed as the first plastic layer is pressed around the mold. The position of the posts can be predetermined to provide rigidity or stability to the disposable container. In some examples, the position of the posts can also be predetermined to preserve a path between the posts to prevent compartmentalizing the disposable container.

In Block 620, a mixture for the mass-rearing of insects is deposited into the cavity. The mixture can include a combination of insect larvae (e.g., mosquito larvae), water, food, and additives. The food can include but is not limited to bread, powdered rice, wheat bran flour, maize, rye, soybean power, dried serum, powdered liver, shrimp powder, skim milk, or Tetramin®. In some examples, the food can be a time-released food (e.g., a food pellet with a coating that dissolves over time to release a portion of the food for consumption). In additional or alternative examples, the food may be deposited periodically throughout the growth cycle of the insects. For example, the top layer may be partially peeled away from the bottom layer to create an opening into the cavity, and additional food can be deposited through the opening.

The amount of mixture added to the cavity can be based on the size of the cavity. For example, an amount of mixture may be selected based on the volume of the cavity to leave room for an air gap between the mixture and the top layer of the disposable container. In some aspects, the size of the air gap can vary based on the type of insect. In some aspects, the mixture can be deposited into the cavity after the cavity is sealed by creating a resealable opening. The resealable opening can be formed by applying a temporary adhesive to the bottom layer at an edge of the cavity. The temporary adhesive can be pressure activated and seal the top layer to the bottom layer in response to pressing the top layer and the bottom layer together at the edge of the cavity. The temporary adhesive can respond to a prying force by allowing the top layer to be separated from the bottom layer at the edge of the cavity and further respond to pressing the top layer to the bottom layer together by resealing at the edge of the cavity. The resealable opening can allow additional food or water to be deposited based on the condition of the larvae. For example, if larvae are under-developing, additional food can be deposited into the disposable container.

In Block 630, a second plastic layer is coupled to the first plastic layer to seal the cavity. A portion of the first layer or a portion of the second plastic layer, or both, can be heated such that the portion of the first layer and the portion of the second layer partially melt and are welded together. In some aspects, an adhesive can be applied for coupling the first plastic layer to the second plastic layer. The cavity can be completely sealed or partially sealed. In additional or alternative aspects, the first plastic layer of the second plastic layer can be gas permeable such that the mixture is sealed in the cavity but air can pass through the disposable container. In some aspects, the second plastic layer can be made from a gas permeable material (e.g., polyisoprene). In additional or alternative aspects, openings can be formed in the second plastic layer small enough to prevent the mixture from passing therethrough but large enough to allow air to pass therethrough.

In some aspects, one or more posts can also be coupled to the second plastic layer to improve the stability or rigidity of the disposable container. After assembly, the disposable container can be transported to a storage area (e.g., by a user or by one or more arms of an automated rearing system). The posts can provide stability such that the disposable container can be carried and positioned on a tray using suction force.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. The phrase "based on" should be understood to be open-ended, and not limiting in any way, and is intended to be interpreted or otherwise read as "based at least in part on," where appropriate. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is otherwise understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present. Additionally, conjunctive language such as the phrase "at least one of X, Y, and Z," unless specifically stated otherwise, should also be understood to mean X, Y, Z, or any combination thereof, including "X, Y, and/or Z."

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A disposable container for the mass-rearing of insects comprising:
    a first layer molded to form a cavity and defining an opening to allow a mixture to be positioned in the cavity;
    a quantity of the mixture positioned in the cavity, the mixture comprising insect larvae and food for the insect larvae; and
    a second layer positioned over the opening and coupled to the first layer to seal the opening,
    wherein the first layer or the second layer comprises a disposable material and the second layer is coupled to the first layer to form the disposable container for the mass-rearing of insects.

2. The disposable container for the mass-rearing of insects of claim 1, wherein the first layer is vacuum molded or blow molded and includes one or more posts extending from the first layer and coupled to the second layer to prevent the cavity from collapsing.

3. The disposable container for the mass-rearing of insects of claim 2, wherein the one or more posts comprise a first post positioned at a first position on the first layer and a second post positioned at a second position on the first layer to form a gap between the first post and the second post.

4. The disposable container for the mass-rearing of insects of claim 2, wherein the second layer is graspable at a position by a vacuum arm, wherein a post of the one or more posts is positioned to couple to the second layer at the position to provide stability for the disposable container.

5. The disposable container for the mass-rearing of insects of claim 1, wherein the first layer comprises a first plastic film and the second layer comprises a second plastic film, the first plastic film or the second plastic film comprising a gas permeable plastic for allowing air to enter the cavity.

6. The disposable container for the mass-rearing of insects of claim 1, wherein the quantity of the mixture positioned in the cavity forms an air gap of approximately 1/16 of an inch to 2 inches between the mixture and the second layer.

7. The disposable container for the mass-rearing of insects of claim 1, wherein the first layer or the second layer comprise a clear material for allowing visual observation of a growth of the insect larvae.

8. The disposable container for the mass-rearing of insects of claim 1, wherein the first layer or the second layer comprise an opaque plastic.

9. The disposable container for the mass-rearing of insects of claim 1, wherein the disposable container for the mass-rearing of insects is positionable in a compartment of a reusable container as a liner.

10. The disposable container for the mass-rearing of insects of claim 1, wherein the disposable container is biodegradable in a release area.

11. The disposable container for the mass-rearing of insects of claim 1, wherein the first layer or the second layer comprises a material that is less than approximately 250 microns thick.

12. A method comprising:
    providing a first layer to be molded to form a cavity and define an opening to allow a mixture to be positioned in the cavity;
    providing a quantity of the mixture to be positioned in the cavity, the mixture comprising insect larvae and food for the insect larvae; and
    providing a second layer to be positioned over the opening and coupled to the first layer for sealing the opening and to form a disposable container for the mass-rearing of insects.

13. The method of claim 12, wherein providing the first layer to be molded further comprises heating the first layer to more than approximately 110 ° C. and vacuum molding or blow molding the cavity to form one or more posts that extend from the first layer and are coupleable to the second layer to prevent the cavity from collapsing.

14. The method of claim 13, wherein providing the first layer to be molded further comprises forming a first post at a first position on the first layer and a second post at a second position on the first layer to form a gap between the first post and the second post.

15. The method of claim 12, wherein providing the first layer to be molded comprises providing a first plastic film, wherein providing the second layer comprises providing a second plastic film, wherein the first plastic film or the second plastic film comprises a gas permeable plastic to allow air to enter the cavity.

16. The method of claim 12, wherein providing the quantity of the mixture comprises defining a top surface of the mixture and forming an air gap between the top surface and the second layer, the air gap being approximately a 1/16 of an inch to 2 inches.

17. The method of claim 12, wherein providing the first layer or providing the second layer comprises providing a clear material to allow visual observation of a growth of the insect larvae.

18. The method of claim 12, wherein providing the first layer or providing the second layer comprises providing an opaque plastic.

19. The method of claim 12, wherein providing the second layer to be coupled to the first layer further comprises forming a biodegradable container to be positioned in a release area to release insects as the biodegradable container degrades.

20. The method of claim 12, wherein providing the first layer or providing the second layer comprises providing a material that is less than approximately 250 microns thick.

* * * * *